United States Patent
Heins et al.

(10) Patent No.: US 6,638,910 B2
(45) Date of Patent: Oct. 28, 2003

(54) COMPOSITIONS AND METHODS FOR CONTROLLING PLANT PESTS

(75) Inventors: Sherry Darlene Heins, Davis, CA (US); Denise Carol Manker, Davis, CA (US); Desmond Rito Jimenez, Woodland, CA (US); Randy Jay McCoy, Davis, CA (US); Pamela Gail Marrone, Davis, CA (US); Jimmy Ensio Orjala, Davis, CA (US)

(73) Assignee: AgraQuest, Inc., Davis, CA (US)

(*) Notice: Subject to any disclaimer, the term of this patent is extended or adjusted under 35 U.S.C. 154(b) by 0 days.

(21) Appl. No.: 09/994,234

(22) Filed: Nov. 27, 2001

(65) Prior Publication Data

US 2003/0186852 A1 Oct. 2, 2003

Related U.S. Application Data (63) Continuation of application No. 09/516,488, filed on Mar. 1, 2000, now Pat. No. 6,417,163, which is a division of application No. 09/223,587, filed on Dec. 30, 1998, now Pat. No. 6,103,228, which is a continuation-in-part of application No. 09/074,870, filed on May 8, 1998, now Pat. No. 6,060,051, which is a continuation-in-part of application No. 08/853,753, filed on May 9, 1997, now abandoned (60) Provisional application No. 60/108,266, filed on Nov. 12, 1998.

(51) Int. Cl.$^7$ .................. A61K 38/00; A01N 63/00; A01N 25/00
(52) U.S. Cl. ................ 514/9; 514/15; 424/93.46; 424/93.462; 424/405
(58) Field of Search ................. 514/9, 15; 424/405, 424/93.46, 93.462

(56) References Cited

U.S. PATENT DOCUMENTS

| | | | |
|---|---|---|---|
| 3,687,926 A | * | 8/1972 | Arima et al. |
| 4,904,585 A | | 2/1990 | Shimada et al. |
| 4,999,192 A | | 3/1991 | Payne et al. |
| 5,045,314 A | | 9/1991 | Bone et al. |
| 5,047,239 A | | 9/1991 | Pusey |
| 5,049,379 A | | 9/1991 | Handelsman et al. |
| 5,055,293 A | | 10/1991 | Aronson et al. |
| 5,061,495 A | | 10/1991 | Rossall |
| 5,187,091 A | | 2/1993 | Donovan et al. |
| 5,208,017 A | | 5/1993 | Bradfisch et al. |
| 5,344,647 A | | 9/1994 | Rossall |
| 5,403,583 A | | 4/1995 | Liu et al. |
| 5,552,138 A | | 9/1996 | Handelsman et al. |
| 5,597,565 A | | 1/1997 | Leifert et al. |
| 5,645,831 A | | 7/1997 | Chilcott et al. |
| 5,733,355 A | * | 3/1998 | Hibino et al. |
| 5,733,544 A | | 3/1998 | Marrone et al. |
| 5,753,222 A | | 5/1998 | Marrone et al. |

FOREIGN PATENT DOCUMENTS

| | | | |
|---|---|---|---|
| DE | 4205196 A1 | | 9/1992 |
| DE | 4205196 | * | 5/1994 |
| JP | 61-051504 | | 9/1987 |
| JP | 62-210996 | | 9/1987 |
| JP | 06135811 A | | 5/1994 |
| JP | 6135811 | * | 5/1994 |
| WO | 96/10083 | | 4/1996 |

OTHER PUBLICATIONS

Argauer et al., "Evidence for novel insecticidally active exotoxin produced by the HD 116 strain of *Bacillus thuringiensis* var, morrison" *J. Entomol. Sci.* 26(2):205–213 (1991).

Arima et al., "Surfactin, A crystalline peptidelipid surfactant produced by *Bacillus subtilis*: Isolation, characterization and its inhibition of fibrin clot formation" *Biochem Biophys. Res. Commun.* 31(3):488–494 (1968).

Asaka et al., "Biocontrol of *Rhizoctonia solani* damping–off of tomato with *Bacillus subtilils* RB14" *Appl. Environ. Microbiol.* 62(11):4081–4085 (1996).

Bakker et al., "Inhibitory effect of *Bacillus subtilis* on *Uromyces phaseoli* and on development of rust pustules on bean leaves" *Phytopathology* 73:1148–1152 (1983).

(List continued on next page.)

*Primary Examiner*—Christopher R. Tate
(74) *Attorney, Agent, or Firm*—Morrison & Foerster LLP (57) ABSTRACT

The present invention relates to a novel antibiotic-producing and metabolite-producing *Bacillus subtilis* strain that exhibits insecticidal, antifungal and antibacterial activity. The supernatant of this novel strain contains effective insecticidal, antifungal and antibacterial agents. Also included in the invention is a solvent extractable, small molecular weight (<10,000 daltons) corn rootworm-active metabolite produced in the supernatant. Also included in the invention are methods of protecting or treating plants from fungal and bacterial infections and corn rootworm infestations comprising the step of applying to the plant an effective amount of the antibiotic/metabolite-producing novel *Bacillus subtilis* strain, the antibiotic/metabolite produced by the novel *Bacillus subtilis* strain or a combination thereof, optionally further comprising another antibiotic-producing bacterial strain and/or a chemical pesticide. The invention also includes methods of preventing or treating fungal and bacterial infections using whole broth cultures or supernatants obtained from cultures of the novel *Bacillus subtilis* stain alone or in combination with chemical pesticides and/or other biocontrol agents. The invention also includes novel antifungal and antibacterial compounds designated agrastatins and a novel combination comprising an A-type iturin, a plipastatin, a surfactin and an agrastatin. Methods of treating or protecting plants from fungal and bacterial infections and corn rootworm infestations comprising administering the novel agrastatins and the novel combination comprising an A-type iturin, a plipastatin, a surfactin and an agrastatin are provided. Further provided is a lipopeptide extract isolated from strain AQ713 with insecticidal activity and a surfactin lipopeptide isolated from strain AQ713 with insecticidal activity.

10 Claims, 2 Drawing Sheets

OTHER PUBLICATIONS

Besson et al., "Antifungal activity upon *Saccharomyces cerevisiae* of iturin A, mycosubtilin, bacillomycin L and of their derivatives: Inhibition of this antifungal activity by lipid antagonists" *J. Antibiotics* 32(8):828–833 (1979).

Bland et al., "Iturin–A, and antifungal peptide produced by *Bacillus subtilis*" *Proc. Plant Growth Regulation Soc. Am.* $22^{nd}$:102–107 (1995).

Bochner, "Sleuthing out bacterial identities" *Nature* 339: 157–158 (1989).

Burgerjon et al., "Alimentation au laboratoire de *Perillus bioculatus* Fabr. avec des larves de *Leptinotarsa decemlineata* intoxiquées par la toxine thermostable de *Bacillus thuringiensis* Berliner" Entomophaga 11:279–284 (1979). An English summary is contained on p. 283.

Cleveland, Jr., "Using cotton marketing alternatives" *Proc.* 1987 *Beltwide Cotton Prod. Conf.*, J.M. Brown, Conf. Coordinator, Dallas, TX, pp. 43–44 (Jan. 4–8, 1987).

Estruch et al., "Transgenic plants: An emerging approach to pest control" *Nature Biotechnol.* 15:137–141 (1997).

Ethridge, "Market pricing based on fiber properties" *Proc.* 1987 *Beltwide Cotton Prod. Conf.*, J.M. Brown, Conf. Coordinator, Dallas, TX, pp. 44–46 (Jan. 4–8, 1987).

Ferreira et al., "Biological control of *Eutypa lata* on grapevine by an antagonistic strain of *Bacillus subtilis*" *Phytopathol.* 81:283–287 (1991).

He et al., "Zwittermicin A, an antifungal and plant protection agent from *Bacillus cereus*" *Tetrahedron Lett.* 35(16):2499–2502 (1994).

Hiraoka et al., "Characterization of *Bacillus subtilis* RB14, coproducer of peptide antibiotics iturin A and surfactin" *J. Gen. Appl. Microbiol.* 38:635–640 (1992).

Huang et al., "Nucleotide sequence and characteristics of the gene Ipa–14, responsible for biosynthesis of the lipopeptide antibiotics iturin A and surfactin from *Bacillus subtilis* RB14" *J. Ferment. Bioeng.* 76(6):445–450 (1993).

Islam et al., "Control of brown spot of rice by *Bacillus megaterium*" *J. Plant Dis. Protect* 92(3):241–246 (1995).

Islam et al., "Inhibition of some fungal pathogens of host phylloplane by *Bacillus megaterium*" *J. Plant Dis. Protect.* 92(3):233–240 (1985).

Johnson et al., "Insecticidal activity of EG4961, a novel strain of *Bacillus thuringiensis* toxic to larvae and adults of Southern corn rootworm (Colcoptera: Chrysomelidae) and Colorado patato beetle (Coleoptera: Chrysomelidae)" *J. Econ. Entomol.* 86:330–333 (1993).

Kakinuma et al., "Determination of fatty acid in surfactin and elucidation of the total structure of surfactin" *Agric. Biol. Chem.* 33(6):973–976 (1969).

Kimura et al., "SNA–60–367, new peptides enzyme inhibitors against aromatase" *J. Antibiotics* 50(6):529–531 (1997).

Latoud et al., "Interactions of antibiotics of the iturin group with human erythrocytes" *Biochem. Biophys. Acta* 856:526–535 (1986).

Leifert et al., "Antiobiotic production and biocontrol activity by *Bacillus subtilis* CL27 and *Bacillus pumilus* CL45" *J. Appl. Bacteriol.* 78:97–108 (1995).

Lüthy, "Insecticidal toxins of *Bacillus thuringiensis*" *FEMS Microbiol. Lett.* 8:1–7 (1980).

Marrone et al., "Improvements in laboratory rearing of the Southern corn rootworm, *Diabrotica undecimpuncta howardi barber* (Coleoptera: Chrysomelidae), on an artificial diet and corn" *J. Econ. Entomol.* 78:290–293 (1985).

McKeen et al., "Production and partial characterization of antifungal substances antagonistic to *Monilinia fructicola* from *Bacillus subtilis*" *Phytopathology* 76(2): 136–139 (1986).

Milner et al., "Production of kanosamine by *Bacillus cereus* UW85" *Appl. Environ. Microb.* 62(8):3061–3065 (1996).

Nishikiori et al., "Plipastatins: New inhibitors of phospholipase $A_2$, produced by *Bacillus cereus* BMG302–fF67" *J. Antibiotics* 39(6):755–761 (1986).

Ohno et al., "Production of antifungal antibiotic, iturin in a solid state fermentation by *Bacillus subtilis* NB22 using wheat bran as a substrate" *Biotech. Lett.* 14(9):817–822 (1992).

Ohno et al., "Effect of temperature change and acration on the production of the antifungal peptide antibiotic iturin by *Bacillus subtilis* NB22 in liquid cultivation" *J. Ferment. Bioeng.* 75(6):463–465 (1993).

Ohno et al., "Effect of temperature on production of lipopeptide antibiotics, iturin A and surfactin by a dual producer, *Bacillus subtilis* RB14, in solid–state fermentation" *J. Ferment. Bioeng.* 80(5):517–519 (1995).

Osburn et al., "Effect of *Bacillus cereus* UW85 on the yield of soybean at two field sites in Wisconsin" *Am. Phytopathol, Soc.* 79(6):551–556 (1995).

Parvin et al., "Cost effectiveness of harvesting at the right time" *Proc.* 1987 *Beltwide Cotton Prod. Conf.*, J.M. Brown, Conf. Coordinator, Dallas, TX, pp. 39–42 (Jan. 4–8, 1987).

Parvin et al., "The economics of cotton harvesting in the midsouth as it relates to shorter season production systems" *Proc..* 1987 *Beltwide Cotton Prod. Conf.*, J.M. Brown, Conf. Coordinator, Dallas, TX, pp. 79–81 (Jan. 4–8, 1987).

Peypoux et al., "Structure de l'iturine C de *Bacillus subtilis*" *Tetrahedron Lett.* 34(8):1147–1152 (1978).

Phae, et al., "Investigation of optimal conditions for foam separation of iturin, and antifungal peptide produced by *Bacillus subtilis*" *J. Ferment. Bioeng.* 71(2):118–121 (1991).

Pusey et al., "Pilot tests for commercial production and application of *Bacillus subtilis* (B–3) for postharvest control of peach brown rot" *Plant Dis.* 72(7):622–626 (1988).

Sandrin et al., "Coproduction of surfactin and iturin A, lipopeptides with surfactant and antifungal properties, by *Bacillus subtilis*" *Biotechnol. Appl. Biochem.* 12:370–375 (1990).

Schwinn et al., "Control with chemicals" *Advances in Plant Pathology: vol.* 7, *Phytophthora infestans*, The Cause of Late Blight of Potato, Academic Press, San Diego Chapter 8, pp. 225–265 (1991).

Sholberg et al., "Biocontrol of postharvest diseases of apple using *Bacillus spp.* Isolated from stored apples" *Can. J. Microbiol.* 41:247–252 (1995).

Singh et al., "*Bacillus subtilis* as a control agent against fungal pathogens of citrus fruit" *Trans. Br. Mycol. Soc.* 83(3):487–490 (1984).

Smith et al., "Suppression of cottony leak of cucumber with *Bacillus cereus* strain UW 85" *Plant Dis.* 77(2):139–142 (1993).

Stabb et al., "Zwittermicin A–producing strains of *Bacillus cereus* from diverse soils" *Appl. Environ. Microbiol.* 60:4404–4412 (1994).

Stonard et al., "Microbial secondary metabolites as a source of agrochemicals" *ACS Symposium Series*, Chapter 3, pp. 25–36 (1994).

Swinburne et al., "Production of antibiotics by *Bacillus subtilis* and their effect on fungal colonists of apple leaf scars" *Trans. Brit. Mycol. Soc.* 65(2):211–217 (1975).

Tsuge et al., "Characterization of *Bacillus subtilis* YB8, coproduce of lipopeptides surfactin and plipastatin B1" *J. Gen. Appl. Microbiol.* 41(6):541–545 (1995).

Umezawa et al., "Plipastatins: New inhibitors of phospholipase $A_2$, produced by *Bacillus cereus* BMG302–fF67" *J. Antibiotics* 39(6):737–744 (1986).

Yamada et al., "Biological activity of antifungal substances produced by *Bacillus subtilis*" *J. Pesticide Sci.* 15(1):95–96 (1990).

Yu et al., "The *Bacillus thuringiensis* Vegetative Insecticidal Protein Vip3A Lyses Midgut Epithelium Cells of Susceptible Insects" *Appl. Environ. Microbiol* 63(2):532–536 (1997).

* cited by examiner

Plipastatin A1, X = Ala, R = $CH_3(CH_2)_{12}-$
Plipastatin A2, X = Ala, R = $CH_3CH_2CHCH_3(CH_2)_{10}-$
Plipastatin B1, X = Val, R = $CH_3(CH_2)_{12}-$
Plipastatin B2, X = Val, R = $CH_3CH_2CHCH_3(CH_2)_{10}-$

COMPOSITIONS AND METHODS FOR CONTROLLING PLANT PESTS

CROSS REFERENCE TO RELATED APPLICATIONS

This application is a continuation of U.S. Ser. No. 09/516,488, filed Mar. 1, 2000, U.S. Pat. No. 6,417,163 which is a divisional of U.S. Ser. No. 09/223,587, filed Dec. 30, 1998, now U.S. Pat. No. 6,103,228, issued Aug. 15, 2000, which is a continuation-in-part of U.S. Ser. No. 09/074,870, filed May 8, 1998, now U.S. Pat. No. 6,060,051, issued Aug. 9, 2000, which is a continuation-in-part of U.S. Ser. No. 08/853,753, filed May 9, 1997, now abandoned. This application also claims priority benefit under 35 U.S.C. §119(e) to U.S. Provisional Application No. 60/108,266, filed Nov. 12, 1998.

FIELD OF THE INVENTION

The present invention is in the field of biopesticides. More particularly, this invention relates to the finding that a novel strain of *Bacillus subtilis*, AQ713, can inhibit a broad range of fungal and bacterial plant diseases and also have activity against insects. The invention also relates to fungicidal, bactericidal, and insecticidal compositions comprising this novel Bacillus strain and the antibiotics and metabolites produced by this strain either alone, or in combination with other chemical and biological pesticides.

BACKGROUND OF THE INVENTION

For a number of years, it has been known that various microorganisms exhibit biological activity so as to be useful to control plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the EPA, are toxic to wildlife and other non-target species. In addition, pathogens may develop resistance to chemical pesticides (see, e.g., Schwinn et al., p. 244, ADVANCES IN PLANT PATHOLOGY: PHYTOPHTHORA INFESTANS, THE CAUSE OF LATE BLIGHT OF POTATO (Academic Press, San Diego 1991).

Every year 250–300 million dollars of chemical pesticides are used to control corn rootworm infestations. Many of these chemical pesticides are toxic to humans, wildlife and other nontarget species. Also some have been found in the ground water. New chemical insecticides cost 100 million to develop.

Biological control offers an attractive alternative to synthetic chemical fungicides. Biopesticides (living organisms and the naturally produced compounds produced by these organisms) can be safer, more biodegradable, and less expensive to develop.

Biopesticides developed from microorganisms are highly desired for integrated pest management programs in agriculture, public health and urban settings. One commonly used biopesticide is the gram positive bacterium *Bacillus thuringiensis*. Pesticidal *B. thuringiensis* strains are known to produce crystal proteins during sporulation, which are specifically toxic to certain orders and species of insects and nematodes (See, e.g., U.S. Pat. No. 4,999,192 and U.S. Pat. No. 5,208,017). Proteinaceous endotoxins produced by *B. thuringiensis* also act as insecticidal agents against corn rootworm and other beetles (e.g., U.S. Pat. No. 5,187,09; Johnson, T. J. et al. (1993), *J. Economic Entomology*, 86: 330–333). *B. thuringiensis* endotoxins have been shown to be effective as purified crystals, washed cell pellets, and expressed proteins. Warren et al. (WO 96/10083), discloses non-endotoxin proteins produced during the vegetative stage of *Bacillus cereus* and *B. thuringiensis*. These vegetative proteins, called Vip1 and Vip2 have potent activity against corn rootworm (northern and western) (Estruch et al. (1997), *Nature Biotechnology* 15:137–141 and Mullins et al. (1997), *Appl. Environ. Microbiol.* 63, (in press).

One *B. thuringiensis* thermostable metabolites, termed beta-exotoxin has also been shown to have pesticidal properties. Burgjeron and Biache (1979), *Entomophaga* 11:279–284 report a beta exotoxin that is active against Colorado potato beetle (*Leptinotarsa decemlineata*). In addition, the known *B. thuringiensis* betaexotoxins exhibits non-specific pesticidal activity, killing not only nematodes, but also flies, armyworms, mites, and corn rootworms. Sigma exotoxin has a structure similar to beta-exotoxin, and is active against Colorado potato beetle (Argauer et al. (1991) *J. Entomol. Sci.* 26:206–213). Alpha-exotoxin is toxic against larvae of *Musca domestica* (Cluthy (1980) *FEMS Microbiol. Lett.* 8:1–7). Gamma-exotoxins are various proteolytic enzymes, chitinases and proteases. The toxic effects of gamma exotoxins are only expressed in combination with beta-exotoxin or delta-endotoxin. Forsberg et al. (1976) "*Bacillus thuringiensis*: Its effects in Environmental Quality," National Research Council of Canada. Stonard et al. (1994) *ACS Symposium Series* 551:25 report a water-soluble secondary metabolite active against corn rootworm in the supernatant of a *Bacillus cereus* strain.

There are no documented strains of *Bacillus subtilis* with broad spectrum insecticidal activity.

Screening programs have identified certain Bacillus spp. (Bacillus spp. includes *B. subtilis, B. cereus, B. mycoides, B. thuringiensis*) strains that exhibit antifungal activity. (See e.g. Stabb et al. (1990) *Applied Environ. Microbiol.* 60: 4404–4412). These strains have been shown to produce zwittermicin-A and or kanosamine (Milner et al. (1996) *Appl. Environ. Microb.* 62: 3061–3066), two antibiotic agents that are effective against the soil borne disease damping off, caused by *Phytophthora medicaginis, P. nicotianae, P. aphanidermatum* or *Sclerotinia minor* (See Stabb et al., supra). Zwittermicin-A is a water soluble, acid stable linear aminopolyol molecule (see, He et al, (1994) *Tetra. Lett.* 35 (16) 2499–2502.

U.S. Pat. No. 5,049,379 to Handelsman et al. describes how zwittermicin-A produces damping off in alfalfa and soybeans. When the seed was coated with *B. cereus* ATCC 53522, the pathogenic activity of root rot fungus is inhibited. Similarly application of spore-based formulations of certain *B. cereus* strains to soybean seeds or the soil surrounding the seeds has been shown to improve soybean yield at field sites. (See, Osburne et al. (1995) *Am. Phytopathol. Soc.* 79(6): 551–556). Methods of applying biopesticides are well known in the art and include, for example, wettable powders, dry flowables, microencapsulation of effective agents, liquid or solid formulations of antibiotic fractions from suitable cultures. (See e.g., U.S. Pat. No. 5,061,495 to Rossall or U.S. Pat. No. 5,049,379 to Handelsman).

Smith et al. (1993) *Plant Disease* 77(2) 139–142 report that the activity of the soil-borne fungus, *Pythium aphanidermatum*, that causes cottony cucumber leak can be suppressed using zwittermicin-producing *B. cereus* strain UW85. Leifert et al. (1995) *J. Appl. Bacteriol.* 78: 97–108 report that the production of anti-Botrytis and anti- Alternaria antibiotics by two Bacillus strains, *B. subtilis* CL27 and *B. pumilis* CL 45. The whole broth and cell-free filtrates were active against Botrytis and Alternaria in in vitro tests and were active against Botrytis in in vivo small plant tests on Astilbe. Leifert et al. (1997) U.S. Pat. No. 5,597,565 disclose *B. subtilis, B. pumilis,* and *B. polymyxa* that are particularly effective at inhibiting post harvest disease causing fungi. They also disclose the presence of antibiotics produced in the cell-free culture filtrate and their activity at different pH values, but they do not identify these compounds.

Rossall (1994) U.S. Pat. No. 5,344,647 discloses *Bacillus subtilis* strains with broad anti-fungal activity. Sholberg et al. (1995) *Can. J. Microbiol.* 41: 247–252, Swinburne et al. (1975) *Trans. Brit. Mycol. Soc.* 65: 211–217, Singh and Deverall (1984) *Trans. Br. Mycol. Soc.* 83: 487–490, and Ferreira, et al. (1991) *Phytopathology* 81: 283–287. Baker et al. (1983) *Phytopathology* 73: 1148–1152 disclose the use of Bacillus spp. and *Bacillus subtilis* as biocontrol agents of fungal plant pathogens. Baker et al. (1983) *Phytopathology* 73: 1148–1152 also report on an antifungal *Bacillus subtilis* for use on plant pathogens. Pusey et al. (1988) *Plant Dis.* 72: 622–626, Pusey and Robins (U.S. Pat. No. 5,047,239), and McKeen et al. (1986) *Phytopathology* 76: 136–139 disclose control of post harvest fruit rot using *B. subtilis*. McKeen et al, supra, have shown that antibiotics similar to the low molecular weight iturin cyclic polypeptides contribute to this fungicidal activity of *B. subtilis*.

Liu et al. (1995) U.S. Pat. No. 5,403,583 disclose a *Bacillus megaterium,* ATCC 55000 and a method to control the fungal plant pathogen, *Rhizoctonia solani*. Islam and Nandi (1985) *Journal of Plant Diseases and Protection* 92(3): 241–246 disclose a *Bacillus megaterium* with antagonism to *Drechslera oryzae*, the causal agent of rice brown spot. The same authors, Islam and Nandi (1985) *Journal of Plant Diseases and Protection* 92(3) 233–240 also disclose in-vitro antagonism of *B. megaterium* against *Drechslera oryzae, Alternaria alternata* and *Fusarium roseum*. They discuss three components in the culture filtrate. The most active antibiotic was highly soluble in water and methanol with a UV peak at 255 nm and a shoulder at 260 nm, which proved to be a polyoxin-like lipopeptide. Cook ((1987) *Proceedings Beltwide Cotton Production—Mechanization Research Conference,* Cotton Council, Memphis, p. 4345) discloses the use of a suspension of *Bacillus megaterium* to reduce the number of cotton plants killed by *Phymatotrichum omnivorum*, a cause of cotton root rot.

Antibiotic production of *B. megaterium* has been recorded by Berdy (CRC Handbook of Antibiotic Compounds, Vols. I–XIV, (CRC Press, Inc. Boca Raton, Fla. 1980–87) who reports production of low-mammalian toxic peptide antibiotics such as ansamitocin-PDM-O, bacimethrin, megacin, pentapeptide, homopeptides.

Bacilli are known to produce antifungal and antibacterial secondary metabolites (Korzybski et al. (1978)). University of Wisconsin and Cornell researchers have identified a novel fungicidal compound, zwittermicin A, produced by Bacillus sp. (He et al. (1994) *Tetra. Lett.* 35(16):2499–2502). A second fungicidal metabolite produced by the same strain was recently identified as the known amino-sugar, kanosamine (Milner et al. (1996) *Appl. Environ. Microb.* 62:3061–3065).

Another group of previously described Bacillus metabolites are the cyclic lipopeptides of the iturin class, some of which are potent fungicidal agents. These agents consist of a cyclic octapeptide with seven α-amino acids and one β-amino acid with an aliphatic side chain. There are several groups of iturins that differ in order and content of the amino acid sequence. These are shown in Table 1 below. Generally, a suite of related molecules is produced with differences in the length and branching of the aliphatic amino acid residue. When tested against *Saccharomyces cerevesiae*, mycosubtilin was found to be the most active agent (LC50=10 μg/mL) followed by iturin-A and bacillomycin L (both having an LC50=30 μg/mL) (Beeson et al. (1979) *J. Antibiotics* 32(8):828–833). The mode of action of these cyclic lipopeptides has been reported to be due to interaction with fungal membranes creating transmembrane channels that permit release of vital ions (Latoud et al. (1986) *Biochem. Biophys. Acta* 856:526–535). Iturin-C is inactive against fungi including *Penicillium chrysogenum* (Peypoux et al. (1978) *Tetrahedron* 34:1147–1152).

TABLE 1

Structures of the iturin family of antibiotics

| Antibiotic | L-Asz(X1) | X4 | X5 | X6 | X7 |
|---|---|---|---|---|---|
| Iturin A | L-Asn | L-Gln | L-Pro | D-Asn | L-Ser |
| Iturin C | L-Asp | L-Gln | L-Pro | D-Asn | L-Ser |
| Bacillomycin D | L-Asn | L-Pro | L-Glu | D-Ser | L-Thr |
| Bacillomycin L | L-Asp | L-Ser | L-Gln | D-Ser | L-Thr |
| Bacillomycin F | L-Asn | L-Gln | L-Pro | D-Asn | L-Thr |
| Mycosubtilin | L-Asn | L-Gln | L-Pro | D-Ser | L-Asn |

$R = CH_3, CH(CH_3)_2, CH_3CH_2CH|CH_3$

A research group at the USDA has investigated the structure/activity relationship of the iturins by synthesizing a number of analogs differing in the amino acid chain length. The researchers reported that the activity of the iturins increased with the length of the fatty acid side chain and the terminal branching in the order iso>normal>anteiso (Bland et al. (1995) *Proc. Plant Growth Regulation Soc. Am.* 22nd: 105–107). They also state that the "amounts of iturins obtained from natural production are inadequate to be commercially viable" based on their work with a number of iturin producing strains of Bacillus.

Figure 1:
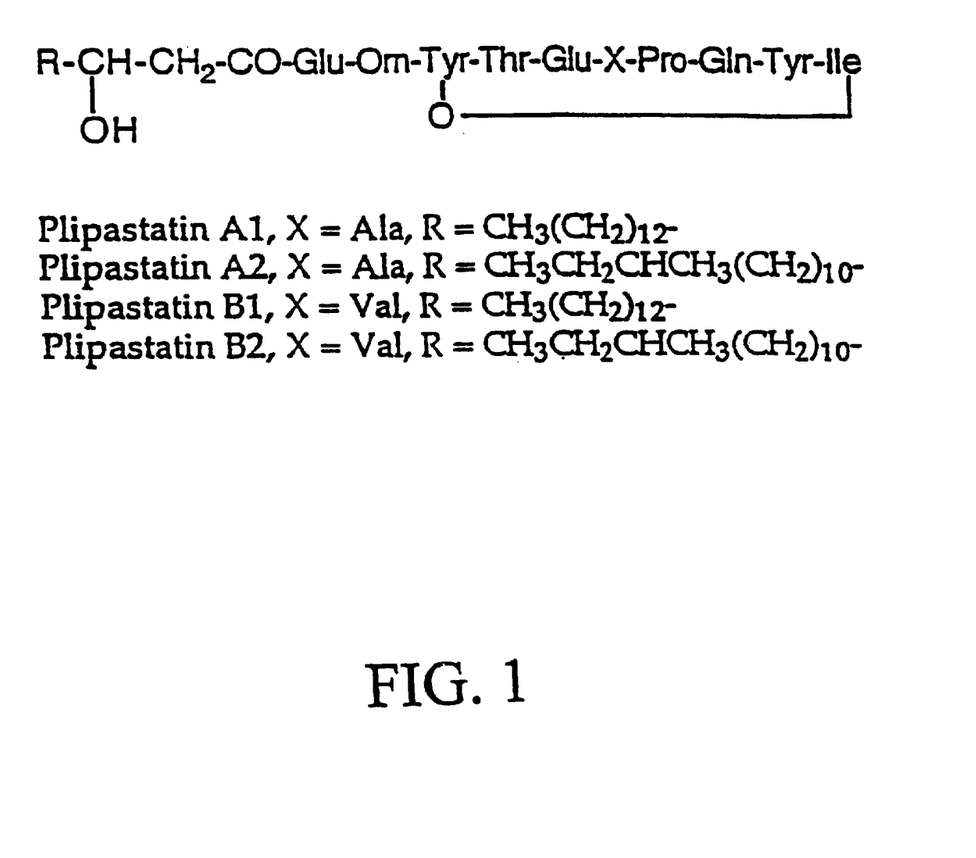
FIG. 1 shows the structure of the plipastatin antibiotics where Plipastatin A1 is SEQ ID NO:2, Plipastatin A2 is SEQ ID NO:3, Plipastatin B1 is SEQ ID NO:4 and Plipastatin B2 is SEQ ID NO:5.
Figure 2:
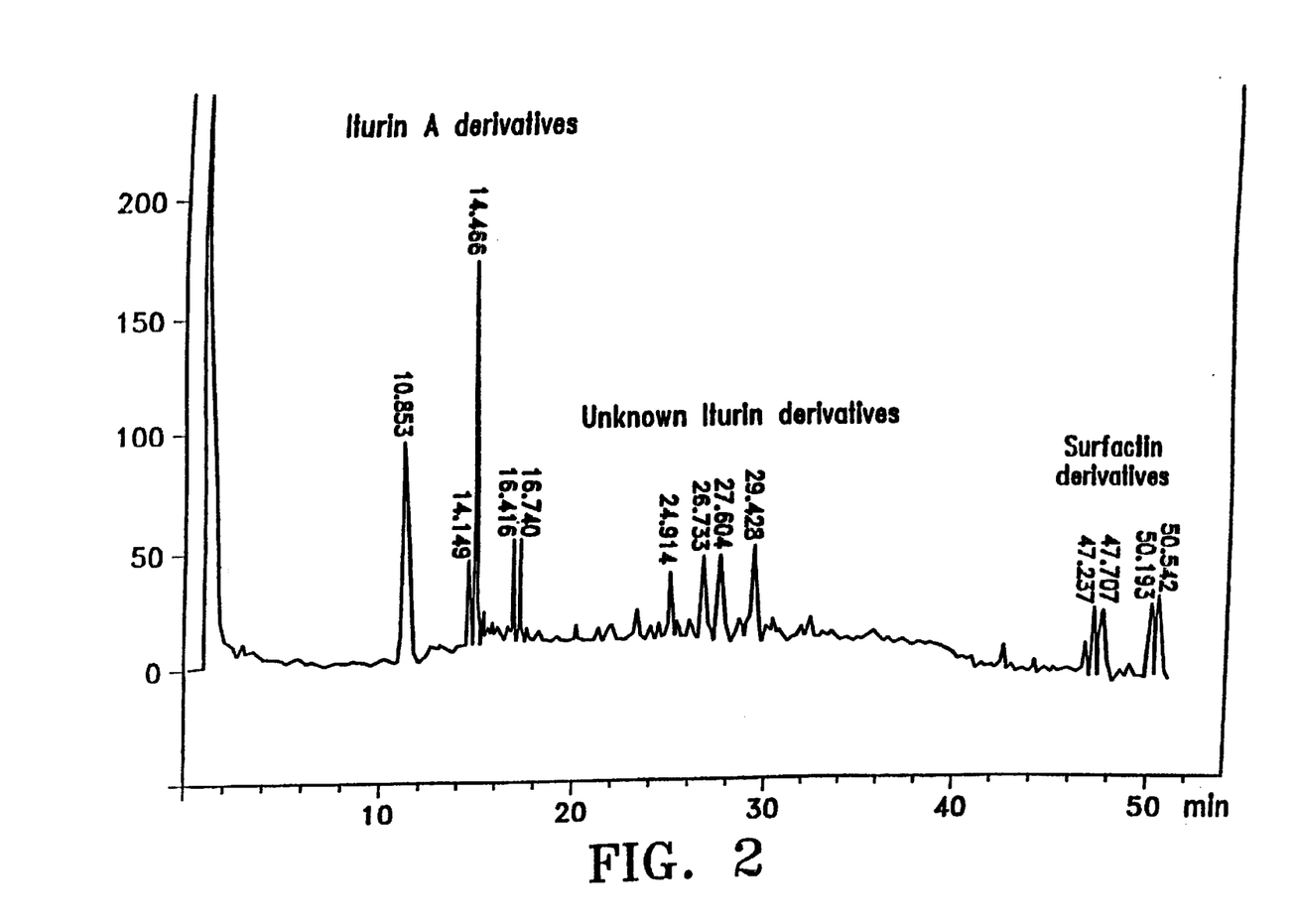
FIG. 2 shows the HPLC chromatogram of AQ713 metabolites.

Another groups of cyclic lipopeptides isolated from *B. cereus* are the plipastatins. These compounds are a family of acylated decapeptides, the structures of which are shown in FIG. 1 (Nishikiori et al. (1986) *J. Antibiotics* 39(6):755–761). These compounds were originally isolated as inhibitors of porcine pancreatic phospholipase $A_2$ (Umezawa et al. (1986) *J. Antibiotics* 39(6):737–744), but were later found to inhibit some plant pathogenic fungi including Botrytis, Pyricularia and Alternaria (Yamada et al. (1990) *Nippon Noyaku Gakkaishi* 15(1):95–96). Yamada also reported a synergistic effect observed between iturin A and the plipastatins, both produced by the same *B. subtilis* strain.

Work has been carried out on fermentation improvements to increase production of the iturins in both liquid (Phae and Shoda (1991) *J. Ferment. Bioeng.* 71:118–121); Ohno et al. (1993) *J. Ferment. Bioeng.* 75:463–465) and solid state fermentations (Ohno et al. (1992) *Biotech. Lett.*

14(9):817–822; Ohno et al. (1995) *J. Ferment. Bioeng.* 5:517–519). There is a report of synergy between the closely related surfactins, that are themselves inactive, and the iturins produced by the same *B. subtilis* strain (Hiraoka et al. (1992) *J. Gen. Appl. Microbiol.* 38:635–640). The nucleotide sequence for the gene that co-regulates biosynthesis of iturin A and surfactin has been published (Huang et al. (1993) *J. Ferment. Bioeng.* 76(6):445–450). Field work on iturin-producing strains has concentrated on soil treatment for control of Rhizoctonia (Asaka and Shoda (1996) *Appl. Environ. Microbiol.* 62:4081–4085) and foliar field applications of iturins have not been reported.

Another cyclic lipopeptide compound produced by *B. subtilis* is surfactin, which possesses an exceptional surfactant activity (Kaninuma et al. (1969) Agric. Biol. Chem. 33:973–976). Surfactin contains a C14 or C15 .beta.-hydroxy fatty acid linked by a lactone ring to a heptapeptide moiety with a LLDLLDL (SEQ ID NO:8) sequence (Arima et al. (1968) Biochem. Biophys. Res. Commun. 31:488–494. Sandrin et al. ((1990) Biotechnol. Appl. Biochem. 12:370–375) found *B. subtilis* strains that produced both surfactin and iturin A, the bacillomycins F and L and mycosubtilin.

The novel microorganism AQ713 discovered by the inventors, previously thought to be a strain of *Bacillus megaterium* and now identified as a strain of *Bacillus subtilis*, produces A iturins, plipastatins and surfactins. Production of this combination of lipopeptides by a microorganism has not been previously reported. In addition, the inventors have discovered that AQ713 also produces a newly described group of compounds designated as "agrastatins." The combination of all three of the above known compounds with the novel agrastatins is also novel Disclosure of the Invention A novel antibiotic-producing and metabolite-producing strain of *Bacillus subtilis*, previously identified as *Bacillus megaterium*, is provided that exhibits broad fungicidal and bactericidal activity and also exhibits insecticidal activity. Also provided is a novel metabolite from the novel *B. subtilis* with activity against foliar and subterranean insects. Also provided is a method of treating or protecting plants from fungal, bacterial and insect infections comprising the step of applying an effective amount of the antibiotic-producing *Bacillus subtilis*. The antibiotic-producing *Bacillus subtilis* can be provided as a suspension in a whole broth culture or as an antibiotic-containing supernatant obtained from a whole broth culture of the antibiotic-producing strain of Bacillus. Also provided is a method of treating or protecting plant roots from subterranean infestations (e.g., corn rootworm) comprising the step of applying an effective amount of the novel metabolite-producing *Bacillus subtilis*, whole broth culture or culture supernatant. The novel metabolite-producing *Bacillus subtilis* can be provided as a suspension in a whole broth culture or as a metabolite-containing supernatant or a purified metabolite obtained from a whole broth culture of the microorganism. Also provided are novel compounds, agrastatins, produced by the novel strain AQ713 and a novel combination of compounds comprising inturin A, a plipastatin, a surfactin and an agrastatin.

MODES OF CARRYING OUT THE INVENTION

The present invention provides a novel strain, AQ713, of *Bacillus subtilis*, previously identified as a *Bacillus megaterium*, or mutants thereof with the broad antifungal, insecticidal and antibacterial activity. This novel strain is designated AQ713 and was deposited with the NRRL on Mar. 7, 1997 under the provisions of the Budapest Treaty on the International Recognition of the Deposit of Microorganisms for the Purpose of Patent Procedure under Accession No. B21661. It was subsequently identified as *Bacillus subtilis* by the American Type Culture Collection (ATCC).

The invention also includes methods of treating plant roots or soil to control insect infestations with a bacterial suspension of AQ713 or a metabolite-containing supernatant of a culture of AQ713 or purified metabolites from strain AQ713.

The invention also includes methods of preventing and treating fungal, bacterial and insect diseases in plants using such bacterial strains or antibiotic-containing supernatants or pure antibiotics obtained from such bacterial strains. The invention also includes methods of treating plant foilage, roots or the soil surrounding the plant to control insects and insect larvae with a bacterial suspension of AQ713 or a metabolite-containing supernatant of a culture of AQ713 or purified metabolites from strain AQ713. The invention also includes a solvent-extractable metabolite with activity on insects with a molecular weight of less than 10,000 daltons. The invention further includes novel compounds, agrastatins, produced by the novel microorganism. Also included is a novel combination comprising an A-type iturin, a plipastatin, a surfactin and an agrastatin.

Definitions

As used herein, "biological control" is defined as control of a pathogen or insect by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may administered so it produces the toxin in situ.

The term "bacteria" includes any prokayotic organism that does not have a distinct nucleus.

The term "fungus" or "fungi" includes a wide variety of nucleated spore-bearing organisms that are devoid of chlorophyll. Examples of fungi include yeast, molds, mildews, rusts, and mushrooms.

"Fungicidal" means the ability of a substance to increase mortality or inhibit the growth rate of fungi.

A "mutant" is an organism bearing a mutant gene that expresses itself in the phenotype of the organism.

"Antibiotic" includes any substance that is able to kill or inhibit a microorganism. Antibiotics may be produced by a microorganism or by a synthetic process or semisynthetic process. The term, therefore, includes a substance that inhibits or kills fungi for example, zwittermicin-A or kanosamine.

"Antifungal" includes any substance that is able to kill or inhibit the growth of fungi.

The term "culturing" refers to the propagation of organisms on or in media of various kinds. "Whole broth culture"

refers to a liquid culture containing both cells and media. "Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the fungal or bacterial disease states.

As used herein, the term "insects" includes all organisms in the class "Insecta". "Pre-adult" insects refers to any form of an organism prior to the adult stage, including, for example, eggs, larvae, and nymphs. "Insecticidal" refers to the ability of a substance to increase mortality or inhibit growth rate of insects. "Nematicidal" refers to the ability of a substance to increase mortality or inhibit the growth rate of nematodes. "Pesticidal" refers to the ability of a substance to increase mortality or inhibit the growth rate of insects, nematodes and mites.

"Positive control" means a compound known to have pesticidal activity. "Positive controls" include, but are not limited to commercially available chemical pesticides. The term "negative control" means a compound known not to have pesticidal activity. Examples of negative controls are water or ethyl acetate.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate.

The term "metabolite" refers to any compound, substance or byproduct of a fermentation of a microorganism that has pesticidal activity. Antibiotic as defined above is a metabolite specifically active against a microorganism.

The term "agrastatins" refers to a group of novel compounds having the following general structures (SEQ ID NO:5):

$$R_1-CH-CH_2-CO-Glx\text{-}Orn\text{-}Tyr\text{-}Thr\text{-}Glx\text{-}X\text{-}Pro\text{-}Glx\text{-}Tyr\text{-}Val$$
$$\quad\ \ |\qquad\qquad\qquad\qquad\quad\ |\qquad\qquad\qquad\qquad\ \ \ |$$
$$\ OR_2\qquad\qquad\qquad\qquad\quad O\text{\textemdash\textemdash\textemdash\textemdash\textemdash\textemdash\textemdash}$$

where $R_1$ is a branched or straight aliphatic side chain, C8–C20; X is either Ala or Val; $R_2$ is an acetate or an ester derivative; and Glx is Gln or Glu. These compounds have broad range antibacterial, anti-insecticidal and antifungal activity.

We describe a novel metabolite and antibiotic-producing strain of *Bacillus subtilis*, previously identified as *Bacillus megaterium*, that has broad antifungal and antibacterial activity and that also kills or stunts insects and their larvae. In another aspect, the present invention provides a method of treating or protecting plants from fungal, insect and bacterial infections comprising applying an effective amount of a supernatant obtained from a whole broth culture of *Bacillus subtilis* AQ713 within the present invention. The supernatant may be obtained well known in the art including centrifugation, filtration, sedimentation and the like.

In another aspect, the invention encompasses a method of treating or protecting plants from fungal, insect and bacterial infections comprising applying an effective amount of the whole broth of the novel strain *Bacillus subtilis*.

In further aspect, the invention encompasses a method of treating or protecting plants from fungal, insect, and bacterial diseases comprising applying an effective amount of the antibiotic produced by the novel strain of *Bacillus subtilis*.

In another aspect, the present invention provides a method of treating or protecting plants and plant roots from insect and larvae infestations comprising applying an effective amount of a supernatant obtained from a whole broth culture of *Bacillus subtilis* AQ713 within the present invention. The supernatant may be obtained well known in the art including centrifugation, filtration, sedimentation and the like.

In another aspect, the invention encompasses a method of treating or protecting plants and plant roots from insect and larvae infestations comprising applying an effective amount of the whole broth of the novel strain *Bacillus subtilis*.

In further aspect, the invention encompasses a method of treating or protecting plant roots from insect infestations comprising applying an effective amount of the metabolite produced by the novel strain of *Bacillus subtilis*.

In order to achieve good dispersion and adhesion of compositions within the, present invention, it may be advantageous to formulate the whole broth culture, supernatant and/or metabolite/antibiotic with components that aid dispersion and adhesion. Suitable formulations will be known to those skilled in the art.

Compositions within the present invention can be formulated as wettable powders, granules and the like, or can be microencapsulated in a suitable medium and the like. Examples of other formulations include, but are not limited to soluble powders, wettable granules, dry flowables, aqueous flowables, wettable dispersible granules, emulsifiable concentrates and aqueous suspensions. Other suitable formulations will be known to those skilled in the art.

In yet a further aspect of the present invention, a novel group of compounds designated "agrastatins" are provided. These compounds exhibit antibacterial and antifungal activity in addition to anti-insect activity.

In still a further aspect of the present invention, a novel combination comprising an A-type iturin, a plipastatin, a surfactin and an agrastatin is provided.

In another aspect of the present invention, methods of treating or protecting plants from insect, fungal and bacterial diseases comprising applying an effective amount of a novel combination of compounds comprising an A-type iturin, a plipastatin, a surfactin and an agrastatin are provided.

Further provided herein is a lipopeptide extract isolated from strain AQ713 with insecticidal activity and a surfactin lipopeptide isolated from strain AQ713 with insecticidal activity. Thus, this invention also provides a method for treating or protecting plants and/or fruits from insect infestations by applying an effective amount of the isolated lipofectin or isolated surfactin to the foilage, roots or the soil surrounding the plants or roots. These isolated compositions can be combined with other known pesticides or insecticides and may be formulated as described above for AQ713 and applied as wettable powders, granules, flowables or microencapsulated.

All patents and publications cited herein are hereby incorporated by reference in their entirety. The following examples are provided to illustrate the invention. These examples are not to be construed as limiting.

EXAMPLES

Example 1

Characterization of Strain AQ713

The isolate was identified based on utilization of the Biolog microplate panel (Biolog, Inc., Hayward, Calif.) as described in Bochner (1989) Nature 339: 157–158. The Biolog microplate is comprised of prefilled and dried panel wells with 95 different carbon substrates plates available for gram positive and gram negative bacteria. The isolate was grown in liquid medium at 28° C. and after 24 hrs a washed cell suspension (0.85% saline) was inoculated into each panel well of a GP Microplate (Biolog, Inc.). After 24 hrs at 28° C., carbon utilization reactions were assessed. Substrate utilization profiles were then compared to the Biolog Gram-Positive Data Base (release 3.50) and isolated to closest similar species. Biolog results gave a similarity index of 0.883 to *Bacillus megaterium*.

A more extensive characterization of AQ713 was conducted by the American Type Culture Collection, (ATCC) 10801 University Blvd., Manassus, Va., 20110-2209.

Isolate submitted as: Unknown; Strain AQ 713

Isolate identified as: Using the available physiological and biochemical data, this strain most closely resembles *Bacillus subtilis*.

Cellular morphology: The motile cells are found in singly, with one endospore formed in the central or subterminal region. The cells are uniformly stained Gram positive.

Colonial morphology: The colonies are opaque and irregular with convex elevation, a rough, dull surface and an erose margin.

| Characterization Data of Strain AQ713: | | | |
|---|---|---|---|
| Rods | + | Colony opaque | + |
| Rods straight | + | Colony entire | − |
| Rods curved | − | Colony erose | + |
| Cells single | + | Colony lobate | − |
| Cells chained | − | Colony circular | − |
| Ends tapered | − | Colony irregular | + |
| Ends rounded | + | Colony rhizoid | − |
| Ends squared | − | Colony low convex | + |
| Endospore formed | + | Colony high convex | − |
| Sporangium swollen | − | Colony flat | − |
| One spore/cell | + | Colony raised | − |
| Spore round | − | Colony glistening | − |
| Spore cylindrical | + | Colony dull | + |
| Spore oval | + | Colony dry | − |
| Spore central | + | Colony smooth | − |
| Spore terminal | − | Colony rough | + |
| Spore subterminal | + | Soluble brown pigment | − |
| Gram stained | + | Soluble black pigment | − |
| Gram positive | + | Soluble yellow pigment | − |
| Gram negative | − | Insoluble brown pigment | − |
| Gram variable | − | Insoluble black pigment | − |
| Vacuoles present | − | Insoluble yellow pigment | − |
| Colony translucent | − | Insoluble orange pigment | − |
| Colony transparent | − | Insoluble red pigment | − |
| Cells motile | + | Acid from lactose | − |
| Growth at 15° C. | + | Gas from lactose | − |
| Growth at 20° C. | + | Acid from mannitol | − |
| Growth at 26° C. | + | Gas from mannitol | − |
| Growth at 30° C. | + | Acid from mannose | − |
| Growth at 37° C. | + | Gas from mannose | − |
| Growth at 45° C. | + | Acid from sucrose | weak |
| Growth at 50° C. | weak | Acid delayed > 14 days | weak |
| Growth at 55° C. | − | Gas from sucrose | − |
| Growth at 60° C. | − | Acid from trehalose | − |
| Growth at 65° C. | − | Gas from trehalose | − |
| Catalase | + | Acid from xylose | − |
| Oxidase | + | Gas from xylose | − |
| Casein hydrolysis | + | Aerobe | − |
| Gelatin liquification | + | Facultative | − |
| Hippurate hydrolysis | − | Microaerophile | + |
| Lecithinase degradation | − | Anaerobe | − |
| Starch hydrolysis | + | Gas from sealed nitrate | − |
| Tween 80 hydrolysis | + | Gas from sealed glucose | − |

| -continued | | | |
|---|---|---|---|
| Characterization Data of Strain AQ713: | | | |
| Tyrosine decomposition | − | Indole | − |
| Growth in 2% NaCl | + | Nitrate to nitrite | + |
| Growth in 5% NaCl | + | Nitrate to gas | − |
| Growth in 7% NaCl | + | Methylene blue reduction | + |
| Growth in 10% NaCl | + | Methylene blue reoxidation | − |
| Growth in 0.2% Na azide | V | Litmus milk acid | − |
| Growth at pH 4.5 | + | Litmus milk coagulated | − |
| Growth at pH 6.0 | + | Litmus milk alkaline | + |
| Acid from arabinose | − | Litmus milk reduced | + |
| Gas from arabinose | − | Litmus Milk peptonized | + |
| Acid from cellobiose | weak | VP (5198) positive | + |
| Acid delayed > 14 days | weak | VP (5331) positive | + |
| Gas from cellobiose | − | pH VP 5198 6.0 or less | − |
| Acid from fructose | + | pH VP 5198 6.5–7.5 | + |
| Acid delayed > 14 days | − | pH VP 5198 8.0 or more | − |
| Gas from fructose | − | Citrate utilization | + |
| Acid from glucose | + | Propionate utilization | − |
| Acid delayed > 14 days | − | Phenylalanine deamination | − |
| Gas from glucose | − | | |

Comments: Using the available physiological and biochemical data, this strain most closely resembles *Bacillus subtilis*.

| Key Characterization Results | | |
|---|---|---|
| Characterization Tests | Strain AQ713 | *Bacillus subtilis* |
| Swollen sporangium | − | − |
| Anaerobic growth | microaerophilic | microaerophilic |
| VP reaction | + | + |
| pH of VP | 7.0 | 5.0–8.0 |
| Maximum temperature growth | 55° C. | 45–55° C. |
| 7% NaCl growth | + | + |
| Acid from glucose | + | + |
| Acid from arabinose | − | + |
| Acid from xylose | − | + |
| Acid from mannitol | − | + |
| Casein decomposition | + | + |
| Tyrosine decomposition | − | − |
| Citrate utilization | + | + |
| Propionate utilization | − | − |

Reference

Gordon, R. E., W. C. Haynes and C. H. N. Pang. 1973. The Genus Bacillus. Handbook No. 427. U.S. Department of Agriculture, Washington, D.C.

Example 2

Activity of AQ713 Against Corn Rootworm

Bacillus samples were grown in a Bacillus culture media. Medium 2 contained 5% peptone, 5% dextrose, 3% yeast extract, 3% malt extract, 1.5% proflo cotton seed extract (59% protein, 4.26% fat, 6.73% ash, 3.19% fiber and trace amounts of gossypol; the balance is water), 10% soy flour, and 0.5% $MgSO_4 \times 7H_2O$. Medium 3 contained the same ingredients, except with 20% peptone and 3.4% $KH_2PO_4$ and 4.3% $K_2HPO_4$. One day old streaked cultures were used to inoculate 250 mL baffled shake flasks. Flasks were shaken at 200 rpm at 29° C. for 5 days. To assay insecticidal activity, 35 mL of culture broth were centrifuged at 5,200 rpm for 20 minutes and the supernatant used in microassay described below.

Assays were performed in 96-well microplates. Each well contained a solid agar substrate, a test organism and either a positive control, a negative control or supernatant obtained as described in Example 1 from the novel Bacillus strain.

To assay insecticidal activity, an agar substrate was prepared for the wells of the microplate according to Marrone et al. (1985), *J. Econ. Entomol.* 78: 290–293. To assay nematicidal activity, plain agar (1.5%) was used in the wells instead.

A 1 ppm solution of Avid® (avermectin) was used as a positive control. Deionized water was used as a negative control. Two replicates of test sample or control were used for each assay. 40 μL of supernatant sample or whole broth grown in medium 1, 2 or 3 were dispensed into each sample well. Plates were then placed in a fume hood to dry for approximately 2–3 hours until the agar solution was dried.

Test organisms were either pre-adult corn rootworms (*Diabrotica undecimpunctata*), pre-adult German cockroaches (*Blatella germanica*), pre-adult beet armyworms (*Spodoptera exigua*), pre-adult flies (*Drosophila melanogaster*), or the N2 strain of the nematode *Caenorhabditis elegans*. Test organisms were diluted in 0.1% agar to a concentration of approximately 5 organisms per 25 μL of agar dispensed into each well. The microplate was sealed with an airtight substance such as Mylar®, and each well ventilated with a pin press. The plates were incubated at 27° C. for up to 7 days.

After incubation, wells were scored by noting neonate mortality or the degree of larval development. Sample wells containing all dead or stunted larvae were given a score of 1, wells containing some dead and other severely stunted larvae were given a score of 2, live but stunted larvae were scored as 3 and sample wells containing no dead larvae were given a score of 4. Scores were averaged among replicates within each sample. Results are summarized in Tables 2 and 3.

TABLE 2

Score Rating of AQ713 Against Insect Pests Whole Broth

| | *C. elegans* | Corn rootworm | Beet armyworm | Fruit Fly | Positive Control | Negative Control |
|---|---|---|---|---|---|---|
| Medium 2 | NT | 1.0 | 4.0 | 4.0 | 1.0 | 4.0 |
| Medium 3 | NT | 2.0 | 4.0 | 4.0 | 1.0 | 4.0 |

NT = not tested

TABLE 3A

Score Rating of AQ713 Against Insect Pests Supernatant Test 1

| | *C. elegans* | Corn rootworm | Beet armyworm | Fruit Fly | German Cockroach | Positive Control | Negative Control |
|---|---|---|---|---|---|---|---|
| Medium 2 | 4.0 | 3.0 | 4.0 | 4.0 | 4.0 | 1.0 | 4.0 |
| Medium 2 | 4.0 | 4.0 | 4.0 | 4.0 | 4.0 | 1.0 | 4.0 |

These tests show that AQ713 was active in both media as a whole broth culture, with the best activity in medium 2. The supernatant was only active when AQ713 was grown in medium 2.

Test Number 2.

AQ713 was tested again against beet armyworm and corn rootworm in a third medium in shake flask or a 10 liter fermenter, called medium 4. It contained the same ingredients as medium 3 without proflo cotton seed extract. All other procedures were the same as above. The test was repeated two or three times.

TABLE 3B

Score Rating of AQ713 Against Insect Pests Supernatant Test

| | Corn rootworm | Beet armyworm | Positive Control | Negative Control |
|---|---|---|---|---|
| Supernatant Medium 4 | 1.0, 1.0, 1.0 | 1.0, 2.0 | 1.0, 1.0, 1.0 | 4.0, 4.0, 4.0 |
| Whole Broth Medium 4 | 1.0, 1.0 | 2.0, 1.0 | 1.0, 1.0 | 4.0, 4.0 |

AQ713 supernatant and whole broth was highly active against corn rootworm and armyworm in medium 4.

Example 3

Activity of AQ713 Against Green Peach Aphids

AQ713 was tested in medium 4 using batches of AQ713 grown twice in two different 10 liter fermenters and twice in one 400 liter fermenters for 48 hours. The green peach aphid, *Myzus persicae* was tested in addition to corn rootworm and armyworm. Both whole broth (WB) and supernatant (S) were tested from one of the 400 liter batches. To test green peach aphid, 40 microliters of the sample of AQ713 were pipetted onto a small filter paper disk at the bottom of each of 8 wells in a 96-well plate. The plates are then dried under a fume hood for 1–2 hours. Aphids are added to each well by gently tapping the aphids off of cabbage leaves. The bottom of the well was covered with aphids. When a column of wells is filled, the plate is capped with a cap strip to keep the aphids in place. The test plates are incubated at 20–22° C. The test is rated in 48 hours, using a microscope to count the number of aphids alive and dead. The wells are then given a score on a scale from 1 to 4 as with the other insects (4 is no dead insects, 1 is 100% kill).

TABLE 4

Score Rating of AQ713 Against Green Peach Aphid Supernatant (S) and Whole Broth (WB) Test

| | | Green Peach Aphid | Positive Control | Negative Control |
|---|---|---|---|---|
| 10 liter (1) | S | 2.0 | 1.0 | 4.0 |
| 10 liter (2) | S | 2.0 | 1.0 | 4.0 |
| 400 liter (1) | S | 1.0 | 1.0 | 4.0 |
| 400 liter (2) | WB | 1.0 | 1.0 | 4.0 |
| 400 liter (2) | S | 1.0 | 1.0 | 4.0 |

This test against small and large fermentations of AQ713 show that both whole broth and supernatant are highly effective at killing green peach aphid.

Example 4

Plant Test of 713 Against Green Peach Aphid

Six inch high pepper plants (Yolo Wonder) were grown in six packs in a greenhouse. The peppers were allowed to be infested naturally from resident green peach aphid populations in the greenhouse. The peppers were sprayed to runoff with a hand held sprayer. AQ713 samples tested were whole broth and spray dried powder of the whole broth grown in a 400 liter fermenter in medium 4. After three days, 75% of the aphids on the AQ713-treated peppers were killed. There were no dead aphids in the untreated or water treated peppers.

Example 5

Chemical Properties of the AQ713 Metabolite Active Against Corn Rootworm 50 mL of AQ713 was grown in media 2. To each culture was added 50 mL ethyl acetate and the mixture was shaken in a separatory funnel for 2 minutes. The aqueous layer was removed and the organic layer was collected in a bottle containing magnesium sulfate. The organic filtrate was then filtered into a round bottom flask and the solvent removed on the rotovap.

For the bioassay, the dried organic extract was redissolved in 2.5 µL acetone. A 40 µL aliquot was removed and diluted to 800 µL with 70% acetone/water. This is a 10×concentration of the organic extract. Serial dilutions were carried out to obtain samples on neonate corn rootworm with percent mortality recorded of neonate larvae (1 per well in a microtiter plate as prepared above) after 7 days. The results are recorded in Table 5.

TABLE 5

Activity of Ethyl Acetate Extracts of AQ713 Against Corn Rootworm

| Sample | | Percent Mortality |
|---|---|---|
| AQ713: | Organic extract 10X | 89 |
| | Organic extract 5X | 93 |
| | Organic extract 1X | 65 |
| | Whole broth | 100 |
| | 70% acetone/water | 27 |
| | Water | 59 |

The results show that AQ713 produces a solvent-extractable metabolite that kills corn rootworms.

To determine the molecular weight range of the active metabolite, a 50 mL culture of AQ713 was grown in media 2. One mL was placed into a microfuge tube and spun at 12,000 rpm for 15 minutes. The supernatant was removed. 500 microliters of supernatant was placed on top of a 10,000 dalton molecular weight centricon filter. These were centrifuged according to the manufacturer's instructions (12,000 rpm for 35 minutes). The filtrate was collected and the retentate recovered by centrifugation and washing of the filter. Samples of the supernatant, filtrate and retentate were tested against neonate corn rootworm larvae (96 well-plate with insect diet, Marrone et al., supra as above; 40 µL of sample per well and 8 wells for each sample, 1 larva/well). The results of the test are shown in Table 6.

TABLE 6

Molecular Weight Cutoff of AQ713

| | | Percent Mortality Against Corn Rootworm |
|---|---|---|
| AQ713: | supernatant | 43 |
| | filtrate | 63 |
| | retentate | 17 |

The results show that the supernatant and filtrate were active, thus the molecular weight of the metabolite is less than 10,000 daltons.

Example 6

Chemical Properties of the AQ713 Metabolite Active Against Plant Pathogens 50 mL of AQ713 was grown in media 2. To each culture was added 50 mL ethyl acetate and the mixture was shaken in a separatory funnel for 2 minutes. The aqueous layer was removed and the organic layer was collected in a bottle containing magnesium sulfate. The organic filtrate was then filtered into a round bottom flask and the solvent removed on the rotovap.

For the bioassay, the dried organic extract was redissolved in 2.5 mL acetone. A 40 µL aliquot was removed and diluted to 800 µL with 70% acetone/water. This is a 10×concentration of the organic extract. A 96-well plate assay (described below) plant pathogen assay with *Pythium ultimum* and *Botrytis cinerea* was conducted to determine activity of the organic extract. The whole broth gave 100% control (score of 1), but the 10×organic extract gave no control of the two plant pathogens (score of 4). This indicates that the active antibiotics, unlike the corn rootworm active metabolites produced by AQ713 are not extractable in an organic solvent such as ethyl acetate.

To extract the active antibiotic fraction and iolate a novel compound, agrastatin A, a butanol extract was made of the fermentation broth by first extracting the broth two times with an equal volume of ethyl acetate and separating the layers. The aqueous fraction was then extracted two times with an equal volume of butanol. The butanol extracts were combined and solvent was removed with a rotary evaporator. A powder was obtained by freeze drying the resulting extract.

The powder was dissolved in 80% acetonitrile/water and sonicated. The solution was applied to a C-18 solid phase extraction (SPE) cartridge that had been activated with methanol and equilibrated with 80% acetonitrile/water. The SPE cartridge was eluted with 80% ACN/water and this eluent was collected and the solvents removed. The eluent was further purified by HPLC. A C-18 HPLC column (1 cm×25 cm) was used (UV detection at 210 nm) with an acetonitrile+0.05% TFA/water+0.05% TFA solvent gradient as follows: 0–20 minutes, 33% ACN; 20–30 minutes, 40% ACN; 30–45 minutes, 45–55% ACN; and 45–63 minutes, 55% ACN.

An HPLC chromatogram of AQ713 shows the presence of the iturins, iturin-like compounds (plipastatins and agrastatins) and surfactins, see FIG. 1. Iturins A2, A3, A4, A7 and A6 were identified by a combination of NMR data and LC mass spectrometry data and comparison to literature values. Surfactins were identified by comparison to purchased surfactin standards by HPLC and by LC mass spectrometry.

The iturin-like compounds were determined to be a mixture of plipastatins and the novel agrastatins by a combination of amino acid analysis and LC mass spectrometry. Extensive NMR data was also collected for one of the novel compounds (HPLC peak 20), designated agrastatin A. Agrastatin A was found to contain the following amino acids: Thr; 3 Glu; Pro; Ala; Val; 2 Tyr; and Orn. This make up differs from plipastatin A by the presence of Val and the loss of Ile. The molecular weight of agrastatin A was determined to be 1448 which corresponds to the following structure (SEQ ID NO: 6):

The straight chain nature of the fatty acid portion was confirmed by $^1$H NMR. The position of the amino acids in the cyclic peptide was determined by detailed analysis of the TOCSY and ROESY datasets.

Mass spectrometry and amino acid analysis of agrastatin B (HPLC peak 26) suggest that its structure is similar to plipastatin B2 with the substitution of the Ala residue with Val. The structure is shown below (SEQ ID NO: 7):

Example 7

Activity of AQ713 Against Plant Pathogens in in-vitro Culture (96-well Plate)

To determine if AQ713 is effective against the fungi, *Phytophthora infestans, Pythium ultimum, Botrytis cinerea, Rhizoctonia solani, Alternaria solani*, the following experiments were performed. 96-well plates (flat-bottomed, 400 microliters per well, Nunc brand) were filled with an agar medium (potato dextrose agar) (PDA, Difco). *Phytophthora infestans* cultures were grown for three days in liquid YPG-1 medium (0.4 g yeast, 0.1% $KH_2PO$, 0.5% $MgSO_4 \times 7H_2O$, 1.5% glucose). For the other fungi, spores were scraped from the surface of petri plates and 0.1–0.2 mL aliquots of deionized water and spore suspension (concentration approximately $2 \times 10^6$ spores/mL) of pathogen were spread onto the agar.

AQ713 was grown for 72 hours in the medium 2 or 3 as described in Example 2. To obtain supernatants, the whole broth culture was centrifuged at 5,200 rpm for 20 minutes. The fungal plant pathogens were pipetted onto the 96-well plates (8 wells/pathogen). The presence or absence of fungal growth was recorded for each of 8 wells. Approximately 40 µL of AQ713 supernatant or 20 µL of whole broth was added to each well. A score of "1" means complete inhibition of fungal growth. A score of "4" means no inhibition of fungal growth. Results are shown in Table 7.

TABLE 7

In-Vitro Inhibition of Fungal Growth (96-well plate)

|  | Media 2 Score | Media 3 Score |
|---|---|---|
| AQ713 Supernatant |  |  |
| *Phytophthora infestans* | 1 | 1 |
| *Pythium ultimum* | 1 | 1 |
| *Botrytis cinerea* | 1 | 1 |
| *Rhizoctonia solani* | 4 | 1 |
| *Alternaria solani* | 1 | 1 |
| AQ713 Whole broth |  |  |
| *Colletotrichum cocodes* | 1 | NT |
| *Alternaria brassicicola* | 1 | NT |
| *Botrytis cinerea* | 1 | NT |
| *Cladosporium cucumerinum* | 1 | NT |
| *Monilinia fructicola* | 1 | NT |
| *Venturia pyrina* | 1 | NT |
| *Rhizoctonia solani* | 1 | NT |
| *Alternaria solani* | 1 | NT |

NT: Not tested

The results show that AQ713 has broad fungicidal spectrum in-vitro and that both the whole broth and supernatant are highly active. The supernatant was active on *Rhizoctonia solani* in medium 3 but not medium 2.

Example 8

Activity of AQ713 Against Plant Pathogens in in-vitro Culture (Zone Assay)

To determine the activity of AQ713 in an agar diffusion (zone) assay, plant pathogen spores were spread over the surface of potato dextrose agar in 10 cm petri dishes. 7.0 mm wells were removed from the agar and a 100 µL sample of the supernatant of AQ713 grown in medium 2 was placed in the well. Supernatant was prepared by centrifuging at 4200 rpm for 40 minutes. The supernatant was then spun again at 4200 rpm for another 40 minutes. Typical results consisted of a zone of no growth and/or reduced growth of the pathogen around the well. The zone size in millimeters was measured and recorded. The results are shown in Table 8.

TABLE 8

In-Vitro Inhibition of Fungal Plant Pathogen Growth (Zone Test)

|  | *Alternaria brassicicola* | *Botrytis cinerea* | *Monilinia fructicola* |
|---|---|---|---|
| AQ713 supernatant Zone size (mm) | 16 | 23 | 14 |
| AQ713 Whole broth | 22 | 15 | 18 |

Example 9

Activity of AQ713 Against Bacterial Plant Pathogens

A standard agar diffusion assay was set up as in Example 6. A lawn of each bacterial pathogen was spread over the surface of a petri plate. 100 µL of AQ713 whole broth grown in medium 2 was placed in each well. The size of the zone was measured in millimeters.

TABLE 9

In-Vitro Inhibition of Bacterial Plant Pathogens (Zone Test)

| AQ713 Whole broth: | Inhibition Zone (mm) |
|---|---|
| *Acidovorax avenae* subsp. *citrulli* | 18 |
| *Pseudomonas syringae* pv. *tomato* | 11 |
| *Xanthomonas campestris* pv. *campestris* | 18 |
| *Erwinia carotovora* subsp. *carotovora* | 11 |
| *Clavibacter michiganense* subsp. *michiganense* | 22 |

AQ713 was active against all species of bacterial plant pathogens tested in-vitro.

Example 10

Activity of AQ713 Against Plant Pathogens in Plant Tests

The activity of AQ713 was tested against gray mold, *Botrytis cinerea*, on beans and geranium leaves, *Alternaria solani* on tomato seedlings, and downy mildew of lettuce, *Bremia lactucae*.

For *A. solani*, tomato seedlings at the 2–3 leaf stage planted in 6-packs were sprayed to runoff with AQ713 whole broth (media 2). After spraying, the seedlings were allowed to dry (about 1.5 hours). The seedlings were then sprayed with $5.0 \times 10^4$ spores/mL. Seedlings were covered with a plastic dome and kept at 28° C. in a Percival incubator. Water with no AQ713, with and without spores of the pathogen was used as a negative control and a positive pathogen control. Four days later the test was read. On the water *A. solani* control, there were uniform lesions over all the leaves and the cotyledons were detached and severely infected (rating of 5=complete infection, no control). AQ713 treated plants had a few light lesions scattered on the true leaves. The cotyledons were attached but with some small lesions (rating of 1). The negative control was not infected.

A second test was set up using detached tomato seedlings (stems broken off at the ground level) placed in mason jars filled with water put under domes and stored as above. The plants were sprayed as above and the symptoms of *A. solani* were recorded four days later. There were no symptoms on the negative control. On the positive control, there were uniform lesions over the seedlings. The AQ713 treatment was rated 1 (few or no lesions). Two days later, the plants in the positive control were destroyed, but the AQ713 treated seedlings were virtually clean and looked the same as the negative controls (water sprayed plants).

For the test on *Botrytis cinerea*, the first true leaves of a bean plant were wounded by pressing the mouth of a 13×100 culture tube onto each leaf. Each leaf received two wounds/leaf. The leaves were sprayed with AQ713 whole broth (media 2) or water alone or the pathogen alone. When dry, they were again sprayed with *B. cinerea* spores ($0.8 \times 10^6$ spores/mL). The leaves were placed in flats covered with plastic domes and stored at 18–20° C. in a Percival incubator. Five days later, the positive control (pathogen alone) was rotted in an area about 25 mm in diameter. The negative control (water alone) had no rotting. AQ713 showed no infections on 7 of 8 circles where the leaves were wounded. The one that was infected had light infection at two locations around the circle.

For the Bremia test, lettuce seeds were planted in a layer of sterilized potting mix containing peat, perlite and vermiculite in small clear plastic plant condominiums about 8 centimeters high and wide. After the lettuce germinated (one week), the lettuce seedlings were sprayed with the AQ713 broth or supernatant sample. The plants were allowed to dry and then downy mildew spore suspension from infected lettuce seedlings was sprayed onto the seedlings. The plastic covers were placed over the plants and incubated at 18–20 20° C. in a Percival incubator. One week later, the test was evaluated. AQ713 did not prevent downy mildew from Bremia on lettuce seedlings.

Example 11

Efficacy of AQ713 Against Plant Diseases
(Greenhouse Test)

Grape Downy Mildew

AQ713 was grown in a soy-based medium in a 400 liter fermenter for 48 hours. Grape plants (cultivar Chardonnay) were sprayed with a hand-held sprayer to run-off with whole broth from the 400 liter fermentation run diluted with sterile water to 0.5× and 0.25×concentrations. When the foliage dried, the plants were sprayed a second time. After drying, the plants were inoculated with the pathogen causing grape downy mildew, *Plasmopara viticola*. Three plants were treated for each dose. Each plant was evaluated by estimating the percent disease control based on a scale from 0 to 100% control. 100% control is a plant with no visible lesions. A chemical fungicide, metalaxyl, was used for comparison. The results were as follows:

| | |
|---|---|
| AQ713 0.5X whole broth | 97.7% control |
| AQ713 0.25X whole broth | 100% control |
| Metalaxyl 30 ppm | 100% control |
| Metalaxyl 10 ppm | 98.3% control |
| Metalaxyl 1 ppm | 80% control |

The results demonstrate that AQ713 effected control of grape downy mildew as well as the chemical fungicide.

Example 12

Efficacy of AQ713 Against Squash Powdery Mildew

AQ713 was grown in a soy-based medium in a 400 liter fermenter for 48 hours. Squash plants (Crookneck and Acorn) were sprayed with a hand-held sprayer to run-off with whole broth from the 400 liter fermentation run and a sample diluted with sterile water to 0.5×concentration. After drying, the plants were inoculated with the squash powdery mildew pathogen, *Sphaerotheca fuliginea*. Two plants were treated for each dose. Spray dried powder of the whole broth was also tested. The 400 liter fermentation broth was spray dried to remove the water. 10% and 2.5% spray dried powder solutions were sprayed on the plants to run-off as above. The incidence of powdery mildew disease was rated on a score from 0 to 5. The 5 rating is 100% disease whereas the 0 rating is no disease. The results are shown below in Table 10.

TABLE 10

| Test Suspension | Acorn Squash Plant 1 | Acorn Squash Plant 2 | Crookneck Squash Plant 1 | Crookneck Squash Plant 2 |
|---|---|---|---|---|
| AQ713 1X whole broth | 0 | 0 | 0 | 0 |
| AQ713 0.5X whole broth | 0 | 0 | 0 | 0 |
| AQ713 10% spray dried powder | 0 | 0 | 0 | 0 |
| AQ713 2.5% spray dried powder | 0 | 0 | 0.5 | 1 |

AQ713 whole broth and spray dried powder provided nearly complete control of squash powdery mildew.

Example 13

Efficacy of AQ713 on Late Blight, Gray Mold, Grape Powdery Mildew, Cereal Powdery Mildew, Sheath Blight and Rice Blast in the Greenhouse AQ713 was grown in a soy-based medium for 72 hours in a 250 mL shake flask. The disease, causative pathogen and host are listed in Table 11 below. This whole broth culture was tested on the plants as shown in Table 11 below.

TABLE 11

| Disease | Plant Pathogen | Host |
|---|---|---|
| Late Blight | *Phytophthora infestans* | Tomato |
| Gray Mold | *Botrytis cinerea* | Pepper |
| Sheath Blight | *Rhizoctonia solani* | Rice |
| Rice Blast | *Pyricularia oryzae* | Rice |

TABLE 11-continued

| Disease | Plant Pathogen | Host |
|---|---|---|
| Powdery Mildew | Uncinula necator | Grape |
| Powdery Mildew | Drysiphe graminis f. sp. graminis | Wheat |

Each broth was sprayed to run-off at 1×concentration on the test plants with a hand held sprayer, allowed to dry and then sprayed a second time. Three plants were treated for each disease and treatment. After drying, the plants were inoculated with the pathogens. Each plant was evaluated by estimating the percent disease control based on a scale from 0 to 100% control 100% control refers to a plant with no visible lesions. Chemical fungicides were used for comparison. Disease index is the severity of the disease on the untreated control.

TABLE 12

| | P. infestans | B. cinerea | E. graminis | U. necator | P. oryzae | R. solani |
|---|---|---|---|---|---|---|
| AQ713 | 70 | 100 | 84 | 100 | 100 | 100 |
| Metalaxy 30 ppm | 100 | | | | | |
| Metalaxyl 10 ppm | 77 | | | | | |
| Propiconazole 10 ppm | | 87 | | | | |
| Propiconazole 5 ppm | | 57 | | | | |
| Propiconazole 0.5 ppm | | | 100 | | | |
| Propiconazole 0.2 ppm | | | 54 | | | |
| Myclobutanil 30 ppm | | | | 100 | | |
| Myclobutanil 10 ppm | | | | 100 | | |
| Pencycuron 50 ppm | | | | | 100 | |
| Pencycuron 10 ppm | | | | | 100 | |
| Benomyl 100 ppm | | | | | | 100 |
| Benomyl 40 ppm | | | | | | 77 |
| Disease Index (%) | 80 | 95 | 70 | 50 | 60 | 80 |

AQ713 showed activity that was equivalent to chemical fungicides on all the pathogens tested.

Example 14

Efficacy of AQ713 Against Brassica Downy Mildew

Bacillus strain AQ713 was grown in a ten liter fermenter in a soy-based medium for 48 hours. The whole broth culture at 1×strength was sprayed onto three week-old cauliflower and brussel sprouts plants at the full cotyledon stage with an artist's air brush powered by compressed air. Three replicates of 15–25 seedlings/pot were sprayed per treatment. Quadris™, an azoxystrobin fungicide from Zeneca, was also sprayed on plants (three per treatment) at rates of 250 ppm and 125 ppm. A spore suspension of downy mildew, Peronospora parasitica, at $1–5×10^4$ spores/mL was sprayed onto the Brassica plants after the AQ713 and Quadris sprays dried. The plants were held at 15–17° C. for 24 hours for infection, then the seedlings were incubated at 20–24° C. for six days. The pots were returned to 15–17° C. overnight to allow sporulation of the pathogen until the test was rated. Each plant was evaluated by estimating the percent disease control based on a scale from 0 to 100% control. 100% control is a plant with no sporulating lesions. The results averaged across replicate pots are shown below in Table 14.

TABLE 14

| | Reading taken December 23 | Reading taken December 30 | Reading taken January 6 |
|---|---|---|---|
| AQ713 whole broth | 100 | 90 | 75 |
| Quadris 250 ppm | 100 | NT | NT |
| Quadris 125 ppm | NT | 100 | 100 |
| Water Control | 0 | 0 | 0 |

NT = Not Tested

AQ713 controlled downy mildew effectively for three weeks in duration.

Example 15

Synergism of AQ713 and a Commercial Fungicide

AQ713 was grown in a ten liter fermenter in a soy-based medium for 72 hours. The bacterial culture was diluted with sterile water to 0.5× and 0.25×concentrations. The culture at 1×, 0.5× and 0.25×concentrations was sprayed onto three week-old pepper plants with an artist's air brush powered by compressed air. Three plants were sprayed per treatment. Quadris™, an azoxystrobin fungicide from Zeneca, was also sprayed on plants (three per treatment) at concentrations of 500 ppm, 250 ppm and 125 ppm. In addition, combinations of Quadris plus the whole broth culture of AQ713 in a 1:1 ratio were sprayed onto pepper plants (three per treatment). The treatments with and without Quadris are outlined in Table 15 below. A spore suspension of Botrytis cinerea, gray mold, at $1×10^6$ spores/mL was sprayed onto the pepper plants after the AQ713 and Quadris sprays dried. The plants were held at 20–22° C. for 3 days until the test was rated. The incidence of gray mold disease was rated on a score from 0 to 5. The 5 rating indicates 100% disease whereas the 0 rating indicates no disease. The results are shown in Table 15 below.

TABLE 15

| Treatment | Rating Replicate 1 | Rating Replicate 2 | Rating Replicate 3 | Rating Average |
|---|---|---|---|---|
| AQ713 1X | 0.5 | 0.5 | 1.5 | 0.8 |
| AQ713 0.5X | 2.0 | 2.5 | 2.0 | 2.2 |
| AQ713 0.25X | 3.0 | 3.0 | 2.0 | 2.7 |
| Quadris 500 ppm | 4.0 | 3.5 | 4.0 | 3.8 |
| Quadris 250 ppm | 2.5 | 3.5 | 3.0 | 3.0 |
| AQ713 1X + Quadris 500 ppm | 0.5 | 1.0 | 1.0 | 0.8 |
| AQ713 1X + Quadris 250 ppm | 1.0 | 1.0 | 0.5 | 0.8 |
| AQ713 0.5X + Quadris 250 ppm | 0.5 | 1.0 | 1.0 | 0.8 |

TABLE 15-continued

| Treatment | Rating Replicate 1 | Rating Replicate 2 | Rating Replicate 3 | Rating Average |
|---|---|---|---|---|
| AQ713 0.25X + Quadris 250 ppm | 0.5 | 1.0 | 2.5 | 1.3 |
| Water control | 4.0 | 5.0 | 5.0 | 4.7 |
| Water control 2 | 5.0 | 5.0 | 5.0 | 5.0 |

The results clearly show that combinations of Quadris and AQ713 control gray mold disease significantly better than either Quadris or AQ713 alone.

Example 16

Determination of the Insecticidal Components of Strain AQ713

The extraction of the lipopeptide fraction (iturins, plipastatins, agrastatins and surfactin) for testing on insects was carried out as follows:

The whole broth is vortexed and the pH is adjusted to 1.5 with HCl, vortexed again, then centrifuged for 15 minutes at 10,500 rpm. The supernatant is poured off and discarded. The pellet is suspended 80% acetonitrile/water (ACN/H$_2$O) and then sonicated for 30 minutes. The sample is centrifuged again for 15 minutes and then the pellet is suspended again in 80% CAN/H$_2$O by vortexing. It is centrifuged again for 15 minutes and then dried in a speed vacuum overnight. The sample is then redissolved in 80% CAN/H$_2$O.

Surfactin, one of the lipopeptides was tested alone. Surfactin was purchased from Sigma Chemicals (St. Louis, Mo.) and is identical to the surfactin in AQ713 as verified by HPLC. Therefore, Sigma surfactin was used in tests against insects.

TABLE 16

Activity of Lipopeptides Against Insect Pests

| | C. Elegans | Corn rootworm | Beet armyworm | Green Peach aphid | Positive Control | Negative Control |
|---|---|---|---|---|---|---|
| Lipopeptide extract | 4.0 | NT | 4.0 | 2.0 | 1.0 | 4.0 |
| Surfactin | 4.0 | 2.0 | 4.0 | 2.0, 3.0, 2.0 | 1.0 | 4.0 |

NT = Not tested

The lipopeptide extract of strain AQ713 is insecticidal. Surfactin alone shows activity against aphids and corn rootworm, but not armyworm. Therefore, the insecticidal activity of strain AQ713 can be partially explained by the lipopeptides in strain AQ713.

While the invention has been described in detail herein and with reference to specific embodiments thereof, it will be apparent to one skilled in the art that various changes and modifications can be made to the invention as described above without departing from the spirit and scope thereof.

What is claimed is:

1. A composition for protecting or treating plants and fruit from fungal and bacterial infections and corn rootworm infestations comprising effective amounts of an iturin A, a plipastatin, a surfactin and an agrastatin.

2. The composition of claim 1, further comprising a chemical fungicide.

3. The composition of claim 1, further comprising a different biological or chemical pesticide or insecticide.

4. The composition of claim 1, further comprising a chemical fungicide.

5. The composition of claim 1, wherein the composition is formulated as a powder, a granule, or a flowable (liquid).

6. The composition of claim 1, wherein the composition is microencapsulated.

7. A method for protecting or treating plants and/or fruit from fungal and bacterial infections and corn root worm infestations comprising applying an effective amount of any of the compositions of claims 1 or 2 to 6 to the plants and/or fruit.

8. The method of claim 7, wherein the infections are caused by at least one microorganism selected from the group consisting of *Phytophthora infestans, Rhizoctonia solani, Pythium ultimum, Botrytis cinerea, Alternaria solani, Colletotrichum cocodes, Alternaria brassicicola, Cladosprorium cucumerinum, Monilinia fructicola, Venturia pyrina, Acidovarax avanae, Pseudomonas syringae, Xanthomonas campestris, Erwinia carotovora, Clavibacter michiganense, Plasmopara viticola, Sphaerotheca fuliginea, Uncinula necator,* and *Peronospora parasitica.*

9. The method of claim 7, wherein the composition comprised of an iturin A, a plipastatin, a surfactin and an agrastatin is applied as wettable powders, granules, flowables or microencapsulations.

10. A method for protecting or treating plants corn rootworm infestations comprising applying an effective amount of any of the compositions of claims 1 or 2 to 3 to roots of plants or to soil around the roots.

* * * * *

SEQUENCE LISTING

```
<160> NUMBER OF SEQ ID NOS: 8

<210> SEQ ID NO 1
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glu has a CH3(CH2)12CH(OH)CH2CO attached
<220> FEATURE:
<221> NAME/KEY: MOD_RES
<222> LOCATION: (2)...(2)
<223> OTHER INFORMATION: Orn

<400> SEQUENCE: 1

Glu Xaa Tyr Thr Glu Ala Pro Gln Tyr Ile
 1               5                  10

<210> SEQ ID NO 2
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glu has a CH3CH2CHCH3(CH2)10CH(OH)CH2CO
      attached.
<220> FEATURE:
<221> NAME/KEY: MOD_RES
<222> LOCATION: (2)...(2)
<223> OTHER INFORMATION: Orn

<400> SEQUENCE: 2
```

```
Glu Xaa Tyr Thr Glu Ala Pro Gln Tyr Ile
 1               5                  10

<210> SEQ ID NO 3
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glu has a RCH(OH)CH2CO attached.
<220> FEATURE:
<221> NAME/KEY: MOD_RES
<222> LOCATION: (2)...(2)
<223> OTHER INFORMATION: Orn

<400> SEQUENCE: 3

Glu Xaa Tyr Thr Glu Val Pro Gln Tyr Ile
 1               5                  10

<210> SEQ ID NO 4
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glu has a CH3(CH2)CHCH3(CH2)10CH(OH)CH2CO
      attached.
<220> FEATURE:
<221> NAME/KEY: MOD_RES
<222> LOCATION: (2)...(2)
<223> OTHER INFORMATION: Orn

<400> SEQUENCE: 4

Glu Xaa Tyr Thr Glu Val Pro Gln Tyr Ile
 1               5                  10

<210> SEQ ID NO 5
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glx has a R1CH(OR2)CH2CO attached, where R1 is
      a branched or straight aliphatic side chain, C8-C20; and R2 is an
      acetate or an ester derivative.
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (6)...(6)
<223> OTHER INFORMATION: Xaa is Ala or Val

<400> SEQUENCE: 5

Glx Xaa Tyr Thr Glx Xaa Pro Glx Tyr Val
 1               5                  10

<210> SEQ ID NO 6
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glu has a CH3(CH2)12CH(OH)CH2CO attached.
<220> FEATURE:
<221> NAME/KEY: MOD_RES
<222> LOCATION: (2)...(2)
```

```
<223> OTHER INFORMATION: Orn

<400> SEQUENCE: 6

Glu Xaa Tyr Thr Glu Ala Pro Gln Tyr Val
 1               5                  10

<210> SEQ ID NO 7
<211> LENGTH: 10
<212> TYPE: PRT
<213> ORGANISM: Bacillus subtilis
<220> FEATURE:
<221> NAME/KEY: MOD_RES
<222> LOCATION: (1)...(1)
<223> OTHER INFORMATION: Glu has a CH3CH2CHCH3(CH2)10CH(OH)CH2CO
      attached.
<220> FEATURE:
<221> NAME/KEY: MOD_RES
<222> LOCATION: (2)...(2)
<223> OTHER INFORMATION: Orn

<400> SEQUENCE: 7

Glu Xaa Tyr Thr Glu Val Pro Gln Tyr Val
 1               5                  10

<210> SEQ ID NO 8
<211> LENGTH: 7
<212> TYPE: PRT
<213> ORGANISM: Bacillus subtilis

<400> SEQUENCE: 8

Leu Leu Asp Leu Leu Asp Leu
 1               5
```